the substituents are as defined herein, the corresponding N-oxides and acid addition salts, a process for their preparation, fungicidal compositions, and their use for controlling harmful fungi.

United States Patent
Wagner et al.

[11] Patent Number: 5,955,473
[45] Date of Patent: Sep. 21, 1999

[54] FUNGICIDAL QUINOLINES

[75] Inventors: Oliver Wagner, Bexbach; Frank Wetterich, Mutterstadt; Karl Eicken, Wachenheim; Gisela Lorenz, Hambach; Eberhard Ammermann, Heppenheim; Siegfried Strathmann, Limburgerhof, all of Germany

[73] Assignee: BASF Aktiengesellschaft, Ludwigshafen, Germany

[21] Appl. No.: 09/029,740

[22] PCT Filed: Sep. 4, 1996

[86] PCT No.: PCT/EP96/03894

§ 371 Date: Mar. 12, 1998

§ 102(e) Date: Mar. 12, 1998

[87] PCT Pub. No.: WO97/10215

PCT Pub. Date: Mar. 20, 1997

[30] Foreign Application Priority Data

Sep. 12, 1995 [DE] Germany .......................... 195 33 653
Sep. 22, 1995 [DE] Germany .......................... 195 35 208

[51] Int. Cl.⁶ ...................... C07D 215/42; C07D 401/12; A01N 43/42
[52] U.S. Cl. ........................... 514/313; 546/159; 546/162
[58] Field of Search ...................... 514/183, 242, 514/245, 255, 256, 275, 247, 313; 544/179, 182, 212, 238, 322, 328, 331, 405; 546/159, 162

[56] References Cited

U.S. PATENT DOCUMENTS 4,801,592  1/1989  Graf et al. .............................. 514/300

FOREIGN PATENT DOCUMENTS

| A-72192/87 | 4/1987 | Australia . |
|---|---|---|
| 0 244 705 | 11/1987 | European Pat. Off. . |
| 0 326 328 | 8/1989 | European Pat. Off. . |
| 0 326 330 | 8/1989 | European Pat. Off. . |
| 0 326 331 | 8/1989 | European Pat. Off. . |
| WO 94 04527 | 3/1994 | WIPO . |

OTHER PUBLICATIONS

Risaliti et al., Chem. Abstract 51:8743, 1957.
Reznikov et al., Chemical Abstract, vol. 123, No. 17, Oct. 23, 1995, 228065u.
Motomizu et al., Chemical Abstract, vol. 117, No. 8, Aug. 24, 1992, 82700z.
Pellerano et al., Chemical Abstract, vol. 84, No. 9, Mar. 1, 1976, 53784z.
Demeunynck et al., Journal of Heterocyclic Chemistry, vol. 21, No. 1, Jan.–Feb. 1984.
Backeberg, Journal of the Chemical Society, London, 1938. Part II., pp. 967–2120.
Kelly et al., Tetrahedron, vol. 41, No. 15, pp. 3033 to 3036, 1985.
Chemical Abstracts, vol. 96, No. 23, Jun. 7, 1982, 199551r.

*Primary Examiner*—Richard L. Raymond
*Assistant Examiner*—Deepak R. Rao
*Attorney, Agent, or Firm*—Oblon, Spivak, McClelland, Maier & Neustadt, P.C.

[57] ABSTRACT

Quinolines of the formula I

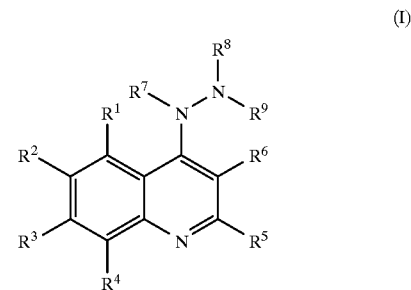

where the substituents are as defined herein, the corresponding N-oxides and acid addition salts, a process for their preparation, fungicidal compositions, and their use for controlling harmful fungi.

12 Claims, No Drawings

FUNGICIDAL QUINOLINES

This application is a 371 of PCT/EP96/03894, filed Sep. 4, 1996.

BACKGROUND OF THE INVENTION

Field of the Invention

The present invention relates to quinolines of the formula I

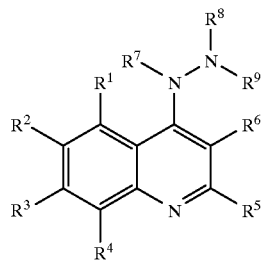

(I)

where the substituents have the following meanings:

$R^1$, $R^2$, $R^3$, $R^4$ in each case independently of one another are hydrogen, hydroxyl, nitro, halogen, $C_1$–$C_4$-alkyl, $C_1$–$C_4$-alkoxy, $C_1$–$C_4$-haloalkyl, $C_1$–$C_4$-alkylthio, $C_1$–$C_4$-haloalkoxy, $C_1$–$C_4$-haloalkylthio, $C_1$–$C_4$-alkoxyalkyl, $R^5$, $R^6$ in each case independently of one another are hydrogen, halogen, $C_1$–$C_4$-alkyl, $C_1$–$C_4$-alkoxy, $C_1$–$C_4$-haloalkoxy, $C_1$–$C_4$-alkylthio;

$R^7$ is hydrogen, $C_1$–$C_4$-alkyl, formyl, $C_1$–$C_4$-alkylcarbonyl, $C_1$–$C_4$-alkoxycarbonyl;

$R^8$ is hydrogen, formyl, $C_1$–$C_8$-alkyl, $C_2$–$C_8$-alkenyl, $C_2$–$C_8$-alkynyl or $C_1$–$C_8$-alkylcarbonyl, it being possible for these groups to be partially or fully halogenated, $C_3$–$C_7$-cycloalkyl or $C_3$–$C_7$-cycloalkenyl, it being possible for these radicals to be partially or fully halogenated, aryl or hetaryl, it being possible for these radicals to have attached to them one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylsulfonyl, $C_1$–$C_4$-alkylsulfoxy, $C_1$–$C_4$-alkylsulfonyloxy, $C_1$–$C_4$-alkylcarbonyl, $C_1$–$C_4$-alkylcarbonyloxy, $C_1$–$C_4$-alkoxycarbonyl, aryl, aryloxy;

$R^7$ and $R^8$ together form a bond;

$R^9$ is aryl or hetaryl, it being possible for these radicals to have attached to them one to three of the following groups: nitro, halogen, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylsulfonyl, $C_1$–$C_4$-alkylsulfoxy, $C_1$–$C_4$-alkylsulfonyloxy, $C_1$–$C_4$-alkylcarbonyl, $C_1$–$C_4$-alkylcarbonyloxy, $C_1$–$C_4$-alkoxycarbonyl, aryl or aryloxy, where the cyclic substituents, in turn, can have attached to them one to three of the following substituents: halogen, nitro, cyano, $C_1$–$C_4$-alkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylsulfonyl, $C_1$–$C_4$-alkylsulfoxy, $C_1$–$C_4$-alkylsulfonyloxy, $C_1$–$C_4$-alkylcarbonyl, $C_1$–$C_4$-alkylcarbonyloxy, $C_1$–$C_4$-alkoxycarbonyl, aryl, aryloxy;

and to the N-oxides and the acid addition salts of the quinolines of the formula I, with the exception of the compounds where the radicals are defined as follows:

| | |
|---|---|
| 1 a–d | $R^{1,2,3,4,5,6,7,8}$ = H; $R^9$ = $C_6H_5$, 4-Cl—$C_6H_4$, 2,4-di-Cl—$C_6H_3$, 2,4-di-Br—$C_6H_3$, |
| 1 e–h | $R^{1,2,3,4,5,6,7,8}$ = H; $R^9$ = 4-Cl—$C_6H_4$, 2,4-di-Cl—$C_6H_3$, in each case in the form of the N-oxide and the HCl salt, |
| 1 i | $R^{1,2,3,4,5,6,7,8}$ = H; $R^9$ = 4-Br—$C_6H_4$ HBr salt |
| 1 j–k | $R^{1,2,3,4,6,8}$ = H; $R^5$ = $CH_3$; $R^7$ = H, $CH_3$; $R^9$ = $C_6H_5$ |
| 1 m | $R^{1,3,4,6,7,8}$ = H; $R^{2,5}$ = $CH_3$; $R^9$ = $C_6H_5$, |
| 1 n | $R^1$ = O—$CH_3$; $R^{2,3,4,6,7,8}$ = H; $R^5$ = $CH_3$; $R^9$ = $C_6H_5$ HCl salt, |
| 1 o–q | $R^{1,3,4,5,6,7,8}$ = H; $R^2$ = $CH_3$; $R^9$ = 4-$NO_2$—$C_6H_4$; HCl salt, N-oxide |
| 1 r–s | $R^{1,2,4,5,6,7,8}$ = H; $R^3$ = Cl; $R^9$ = 4-$NO_2$—$C_6H_4$, 4-Cl—$C_6H_4$ |
| 1 t–u | $R^{1,2,3,4,6,7,8}$ = H; $R^5$ = Cl; $R^9$ = 4-Cl—$C_6H_4$, 2,4-di-Cl—$C_6H_3$ |
| 1 v–x | $R^{1,4,6,7}$ = H; $R^3$ = H,; $R^2$ = H,$CH_3$O; $R^5$ = $CH_3$ $R^{8,9}$ = $CH_2CH_2Cl$ HCl salt, |
| 1 x | $R^{1,4,6,7}$ = H; $R^3$ = Cl $R^2$ = H; $R^5$ = $CH_3$ $R^{8,9}$ = $CH_2CH_2Cl$ HCl salt, |
| 1 y | $R^{1,4,6,7}$ = H; $R^3$ = H; $R^2$ = Cl; $R^5$ = H $R^{8,9}$ = $CH_2CH_2Cl$ HCl salt, |
| 1 z | $R^{1,2,4,5,6,7,8}$ = H; $R^3$ = Cl; $R^9$ = $CH_2$-3-Py, |
| 2 a–b | $R^{1,2,3,4,5,6,7,8}$ = H; $R^9$ = quinolin-4-yl, di-N-oxide, |
| 2 c | $R^{1,2,3,4,6,7,8}$ = H; $R^5$ = $CH_3$; $R^9$ = quinolin-4-yl, di-N-oxide, |
| 2 d–o | $R^{1,2,3,4,5,6}$ = H; $R^9$ = $C_6H_5$, $C_6H_5$ N-oxide, 4-Cl—$C_6H_4$, 4-Cl—$C_6H_4$ N-oxide, 4-Br—$C_6H_4$, 4-Br—$C_6H_4$ N-oxide, 2,4-Cl—$C_6H_3$, 2,4-Cl—$C_6H_3$ N-oxide, 2,4-Br—$C_6H_3$, 2,4-Br—$C_6H_3$ N-oxide, 4-$(CH_3)_2$N—$C_6H_4$, 4-$(CH_3)_2$N—$C_6H_4$ N-oxide, |
| 2 p–q | $R^{1,3,6}$ = H; $R^5$ = $CH_3$, $R^9$ = $C_6H_5$; $R^2$ = $OCH_3$, $R^4$ = $OCH_3$; |
| 2 r–s | $R^{1,3,6}$ = H; $R^5$ = $CH_3$; $R^9$ = $C_6H_5$; $R^2$ = $OCH_2CH_3$; $R^4$ = $OCH_2CH_3$; |
| 2 t–v | $R^{1,2,3,4,6}$ = H; $R^5$ = Cl; $R^9$ = $C_6H_5$, 4-Cl—$C_6H_4$, 2,4-Cl—$C_6H_3$, |
| 2 w | $R^{1,2,4,5,6}$ = H; $R^3$ = Cl; $R^9$ = $C_6H_5$, |
| 2 x | $R^{1,2,3,4,6}$ = H; $R^5$ = $CH_3$; $R^9$ = $C_6H_5$, |
| 2 y | $R^{1,2,3,4}$ = H; $R^{5,6}$ = $CH_3$; $R^9$ = $C_6H_5$, |
| 2 z | $R^{2,3,4,6}$ = H; $R^{1,5}$ = $CH_3$; $R^9$ = $C_6H_5$, |
| 3 a | $R^{1,3,4,6}$ = H; $R^{2,5}$ = $CH_3$; $R^9$ = $C_6H_5$, |
| 3 b | $R^{1,2,3,6}$ = H; $R^{4,5}$ = $CH_3$; $R^9$ = $C_6H_5$, |
| 3 c | $R^{2,4,6}$ = H; $R^{1,3,5}$ = $CH_3$; $R^9$ = $C_6H_5$, |
| 3 d | $R^{1,3,6}$ = H; $R^{2,4,5}$ = $CH_3$; $R^9$ = $C_6H_5$, | to a process for their preparation, to fungicidal compositions, and to their use for controlling harmful fungi.

DESCRIPTION OF THE BACKGROUND

WO 94/07492 discloses 4-hydrazinoquinolines and 4-hydrazonoquinolines which are pharmaceutically active.

While 4-quinolinehydrazines are disclosed in the literature, a fungicidal action of these compounds is not reported (cf.: Ann. Chim.(Rome), 46(1956)1050; J. Chem. Soc., 1930, 1999; J. Chem. Soc., 1938, 1083; Yakugaku Zasshi, 65(1945)Ed. B, 431; Farmaco, Ed. Sci., 30 (1975) 965), J. Med. Chem., 12 (1969) 801.

Various phenylazoquinolines are also described in the literature (cf. J. Heterocyclic Chem.; 21 (1984) 501; Ann. Chim.(Rome), 46(1956)1050; J. Chem. Soc; 1084, 1938).

Attl. Accad. Sci. Siena Fisiocrit. (1976) 8, 43–57 reports 4-hydrazonoquinolines which have a microbicidal action. However, these compounds are not reported as having a fungicidal action against plant pathogens.

SUMMARY OF THE INVENTION

It was an object of the present invention to provide quinoline derivatives which have a fungicidal action.

We have found that this object is achieved by compounds of the formula I, which have a good fungicidal activity against plant pathogens.

DETAILED DESCRIPTION OF THE INVENTION

The compounds of the present invention can be prepared by applying known syntheses. The starting compounds can be obtained by known methods.

The compounds of the general formula I are obtained by subjecting the 4-chloroquinolines of the formula II to a condensation reaction with hydrazines of the formula III.

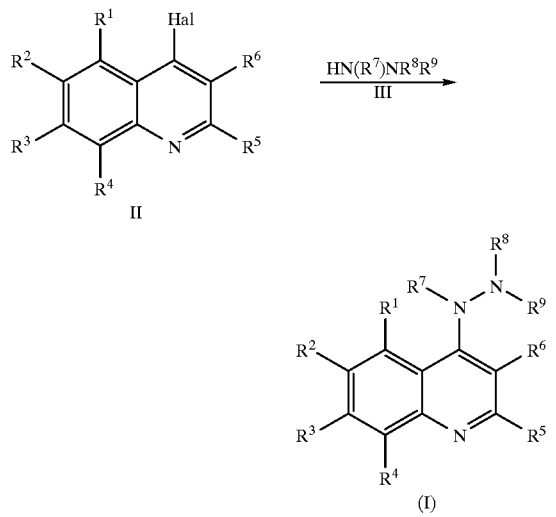

Those quinolines II which are not already known can be obtained by known methods (Tetrahedron 41 (1985) 3033–36, Organic. Syntheses, Col. Vol.3,272 (1955), EP 497371, U.S. Pat. No. 5,240,940).

Those hydrazines III which are not already known can also be obtained by known methods (cf. Houben-Weyl, Volume 10/2, pages 1 to 71 and 169–409, especially 396–399 and 402–405).

The compounds of the general formula I are obtained by subjecting the 4-chloroquinolines II to a condensation reaction with hydrazines of the formula III.

The 4-chloroquinolines II are preferably reacted with the hydrazines in question at elevated temperatures in a suitable diluent. Suitable diluents are inert organic solvents, such as aliphatic hydrocarbons, eg. petroleum ether, aromatic hydrocarbons, eg. toluene or o-, m- or p-xylene, or else alcohols, eg. n-, i- or t-butanol.

The invention also encompasses the salts of the compounds I, in particular the salts of mineral acids or Lewis acids. The type of the salt is normally not critical. Preferred for the purposes of the invention are those salts which do not damage the plants, areas, materials or spaces to be kept free from harmful fungi and which do not adversely affect the activity of the compounds I.

The salts of the compounds I are accessible in a manner known per se, for example by reacting the relevant quinolines I with acids in water or an inert organic solvent at from −80° to 120°, preferably 0° to 60° C.

The invention also encompasses the N-oxides of the compounds I. They can be prepared by methods known from the literature (see, for example, Ann. Chim. Rome; 46(1956) 1050).

Compounds Ia where $R^7$, $R^8$ are a bond can be prepared by methods known from the literature (see Houben-Weyl; Volume 10/3, pages 226–423), for example by coupling aromatic diazonium compounds (p. 226–311), by means of condensation reactions (p. 332–355) or by dehydrating the compounds of the general formula Ib where $R^7$ and $R^8$ are hydrogen (p. 377).

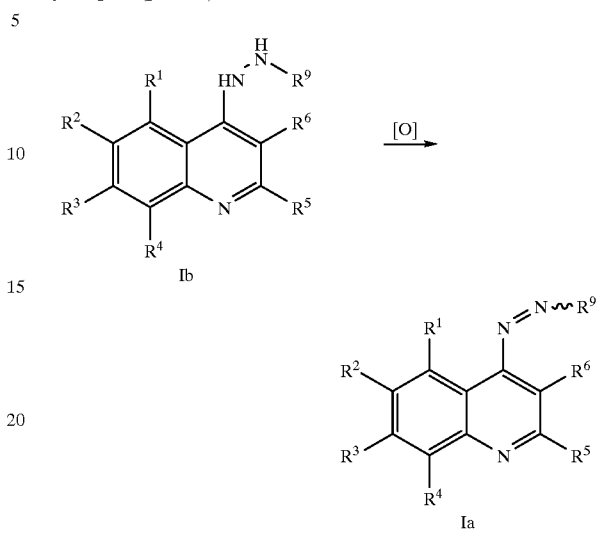

Suitable oxidants are inorganic and organic compounds, eg. peroxides, hypohalites, nitrous acid, nitric acid, metal salts, eg. Fe(III) salts, Cu(II) salts, Pb(IV) salts, but also oxygen or air.

Examples of suitable diluents are water, organic and inorganic acids, eg. glacial acetic acid, sulfuric acid or nitric acid; alcohols, eg. methanol or ethanol; halogenated hydrocarbons, aromatic hydrocarbons or else dimethylformamide.

The reaction temperature is generally from 0° to the boiling point of the solvent in question.

Collective terms which represent the following substituents were used for the definitions of the compounds I given at the outset:

halogen: fluorine, chlorine, bromine and iodine;

alkyl: straight-chain or branched alkyl groups having 1 to 8 carbon atoms, eg. $C_1$–$C_6$-alkyl, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl, or partially or fully halogenated alkyl: straight-chain or branched alkyl groups having 1 to 4 or 8 carbon atoms (as mentioned above), it being possible for the hydrogen atoms in these groups to be partially or fully replaced by halogen atoms (as mentioned above), eg. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkoxy groups having 1 to 4 carbon atoms, eg. $C_1$–$C_3$-alkoxy, such as methyloxy, ethyloxy, propyloxy and 1-methylethyloxy;

alkoxyalkyl: straight-chain or branched alkyl groups having 1 to 8 carbon atoms (as mentioned above) which have attached to them in any position a straight-chain or branched alkoxy group (as mentioned above) having, in the case of $C_1$–$C_4$-alkoxyalkyl, 1 to 4 carbon atoms, such as methoxymethyl, ethoxymethyl, n-propoxymethyl, n-butoxymethyl, 1-methoxyethyl, 2-methoxyethyl, 1-ethoxyethyl, 2-ethoxyethyl, 2-n-propoxyethyl and 2-butoxyethyl;

haloalkoxy: straight-chain or branched alkoxy groups having 1 to 4 carbon atoms (as mentioned above), it being possible for the hydrogen atoms in these groups to be partially or fully replaced by halogen atoms (as mentioned above), eg. $C_1$–$C_2$-haloalkoxy, such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy;

alkylthio: straight-chain or branched alkyl groups having 1 to 4 carbon atoms (as mentioned above) which are bonded to the skeleton via a sulfur atom (—S—), eg. $C_1$–$C_4$-alkylthio, such as methylthio, ethylthio, propylthio, 1-methylethylthio, n-butylthio and tert-butylthio;

alkoxycarbonyl: straight-chain or branched alkoxy groups having 1 to 4 C atoms (as mentioned above) which are bonded to the skeleton via a carbonyl group (—CO—);

alkenyl: straight-chain or branched alkenyl groups having 2 to 8 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 2-methyl-1-propenyl, 1-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched alkynyl groups having 2 to 8 carbon atoms and a triple bond in any position, eg. $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic alkyl groups having 3 to 7 carbon ring members, eg. $C_3$–$C_7$-cycloalkyl, such as cyclopropyl, cyclobutyl, cyclopentyl, cyclohexyl and cycloheptyl;

cycloalkenyl: monocyclic alkyl groups having 5 to 7 carbon ring members which contain one or more double bonds, eg. $C_5$–$C_7$-cycloalkenyl, such as cyclopentenyl, cyclohexenyl and cycloheptenyl;

non-aromatic 4- to 8-membered rings which, besides carbon, additionally contain one or two oxygen, sulfur or nitrogen atoms as ring members, such as saturated 5- or 6-membered rings having 1 or 2 nitrogen and/or oxygen atoms, such as 3-tetrahydrofuranyl, 1-piperidinyl, 2-piperidinyl, 3-piperidinyl, 4-piperidinyl, 2-tetrahydropyranyl, 3-tetrahydropyranyl, 4-tetrahydropyranyl, 2-morpholinyl and 3-morpholinyl;

aryl: monocyclic or polycyclic aromatic groups having 6 to 10 C atoms, such as phenyl and naphthyl;

arylalkyl: aryl groups (as mentioned above) which, in the case of aryl($C_1$–$C_4$)alkyl, are bonded to the skeleton via alkyl groups having 1 to 4 carbon atoms (as mentioned above), eg. phenyl($C_1$–$C_4$)alkyl, such as benzyl, 2-phenylethyl, 3-phenylpropyl, 4-phenylbutyl, 1-phenylethyl, 1-phenylpropyl and 1-phenylbutyl;

aryloxy: aryl groups (as mentioned above) which are bonded to the skeleton via an oxygen atom (—O—), such as phenoxy, 1-naphthoxy and 2-naphthoxy;

hetaryl: aromatic mono- or polycyclic radicals which, besides carbon ring members, can additionally contain 1 to 4 nitrogen atoms or 1 to 3 nitrogen atoms and one oxygen or one sulfur atom or one oxygen or one sulfur atom, eg.:

5-membered hetaryl containing 1 to 3 nitrogen atoms: 5-membered hetaryl ring groups which, besides carbon atoms, can contain 1 to 3 nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing 1 to 4 nitrogen atoms or 1 to 3 nitrogen atoms and 1 sulfur atom or oxygen atom or 1 oxygen or 1 sulfur atom: 5-membered hetaryl ring groups which, besides carbon atoms, can contain 1 to 4 nitrogen atoms or 1 to 3 nitrogen atoms and 1 sulfur or oxygen atom or 1 oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl containing 1 to 3 nitrogen atoms or 1 nitrogen atom and/or one oxygen or sulfur atom: 5-membered hetaryl ring groups which, besides carbon atoms, can contain 1 to 4 nitrogen atoms or 1 to 3 nitrogen atoms and 1 sulfur or oxygen atom or 1 oxygen or one sulfur atom as ring members and in which 2 adjacent carbon ring members or 1 nitrogen and 1 adjacent carbon ring member can be bridged by a buta-1,3-diene-1,4-diyl group;

5-membered hetaryl bonded via nitrogen and containing 1 to 4 nitrogen atoms, or benzo-fused 5-membered hetaryl bonded via nitrogen and containing 1 to 3 nitrogen atoms: 5-membered hetaryl ring groups which, besides carbon atoms, can contain 1 to 4 nitrogen atoms, or 1 to 3 nitrogen atoms, respectively, as ring members and in which 2 adjacent carbon ring members or one nitrogen and one adjacent carbon ring member can be bridged by a buta-1,3-diene-1,4-diyl group, these rings being bonded to the skeleton via one of the nitrogen ring members;

6-membered hetaryl containing 1 to 3, or 1 to 4, respectively, nitrogen atoms: 6-membered hetaryl ring groups which, besides carbon atoms, can contain 1 to 3, or 1 to 4, respectively, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl containing 1 to 4 nitrogen atoms: 6-membered hetaryl ring groups in which 2 adjacent carbon ring members can be bridged by a buta-1,3-diene-1,4-diyl group, eg. quinoline, isoquinoline, quinazoline and quinoxaline.

The term "partially or fully halogenated" is to express that in groups which are thus characterized some or all of the hydrogen atoms can be replaced by identical or different halogen atoms as mentioned above.

Alkylamino: an amino group which has attached to it a straight-chain or branched alkyl group having 1 to 6 carbon atoms as mentioned above;

dialkylamino: an amino group which has attached to it two straight-chain or branched alkyl groups which are independent of one another and have attached to them in each case 1 to 6 carbon atoms as mentioned above;

alkylcarbonyl: straight-chain or branched alkyl groups having 1 to 10 carbon atoms which are bonded to the skeleton via a carbonyl group (—CO—);

alkylsulfonyl: straight-chain or branched alkyl groups having 1 to 6 or 10 carbon atoms which are bonded to the skeleton via a sulfonyl group (—SO$_2$—);

alkylsulfoxyl: straight-chain or branched alkyl groups having 1 bis 6 carbon atoms which are bonded to the skeleton via a sulfoxyl group (—S(=O)—);

alkylsulfonyloxy: straight-chain or branched alkyl groups having 1 to 6 or 10 carbon atoms which are bonded to the skeleton via a sulfonyloxy group (—SO$_2$—O);

alkylcarbonyloxy: straight-chain or branched alkyl groups having 1 to 10 carbon atoms which are bonded to the skeleton via a carbonyloxy group (—CO—O);

alkoxycarbonyl: straight-chain or branched alkyl groups having 1 bis 6 carbon atoms which are bonded to the skeleton via a oxycarbonyl group (—OC(=O)—).

Compounds I which are preferred regarding their biological action against harmful fungi are those where $R^1$, $R^2$, $R^3$, $R^4$ in each case independently of one another are hydrogen, halogen, $C_1$–$C_4$-alkyl, $C_1$–$C_4$-alkoxy, $C_1$–$C_4$-haloalkyl, $C_1$–$C_4$-alkylthio, $C_1$–$C_4$-haloalkoxy, $C_1$–$C_4$-haloalkylthio, $C_1$–$C_4$-alkoxyalkyl, $R^5$ and $R^6$ in each case independently of one another are hydrogen, $C_1$–$C_2$-alkyl or halogen $R^7$ and $R^8$ in each case independently of one another are hydrogen, $C_1$–$C_6$-alkyl, $C_1$–$C_3$-alkylcarbonyl, formyl $R^7$, $R^8$ together are a bond, $R^9$ is aryl or hetaryl, it being possible for these radicals to have attached to them one to three of the following groups: nitro, halogen, cyano, $C_1$–$C_4$-alkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylsulfonyl, $C_1$–$C_4$-alkylsulfoxy, $C_1$–$C_4$-alkylsulfonyloxy, $C_1$–$C_4$-alkylcarbonyl, $C_1$–$C_4$-alkylcarbonyloxy, $C_1$–$C_4$-alkoxycarbonyl, aryl or aryloxy, where the cyclic substituents, in turn, can have attached to them one to three of the following substituents: halogen, nitro, cyano, $C_1$–$C_4$-alkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylsulfonyl, $C_1$–$C_4$-alkylsulfoxy, $C_1$–$C_4$-alkylsulfonyloxy, $C_1$–$C_4$-alkylcarbonyl, $C_1$–$C_4$-alkylcarbonyloxy, $C_1$–$C_4$-alkoxycarbonyl, aryl, aryloxy.

Particularly preferred compounds I are those where the radicals have the following meanings, either on their own or in combinations:

two of the radicals $R^1$, $R^2$, $R^3$, $R^4$ are hydrogen;

three of the radicals $R^1$, $R^2$, $R^3$, $R^4$ are hydrogen;

$R^3$=cyano, halogen, $C_1$–$C_3$-alkyl, $C_1$–$C_3$-alkyloxy, $C_1$–$C_3$-alkylthio, $C_1$–$C_3$-haloalkoxy; preferably halogen, $C_1$–$C_3$-alkyl, in particular chlorine and methyl;

$R^5$ and $R^6$ are hydrogen, halogen, methyl, especially hydrogen;

$R^5$ is hydrogen, methyl, chlorine, especially hydrogen;

$R^6$ is hydrogen;

$R^7$ is hydrogen, methyl, formyl, $C_1$–$C_2$-alkylcarbonyl, especially hydrogen;

$R^7$ and $R^8$ are hydrogen, $C_1$–$C_6$-alkyl, $C_4$–$C_6$-cycloalkyl, formyl, $C_1$–$C_2$-alkylcarbonyl;

$R^8$ is hydrogen, formyl, $C_1$–$C_2$-alkylcarbonyl, $C_1$–$C_4$-alkyl, $C_4$–$C_6$-cycloalkyl; especially preferably hydrogen, formyl, $CH_3CO$, $C_1$–$C_4$-alkyl; furthermore preferably hydrogen, $C_1$–$C_4$-alkyl, especially preferably hydrogen, methyl, ethyl, i-propyl, n-butyl, especially hydrogen;

$R^7$ and $R^8$ especially preferably form a joint bond;

$R^9$ is aryl, it being possible for these radicals to have attached to them one to three of the following groups: nitro, halogen, cyano, $C_1$–$C_4$-alkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylsulfonyl, $C_1$–$C_4$-alkylsulfoxy, $C_1$–$C_4$-alkylsulfonyloxy, $C_1$–$C_4$-alkylcarbonyl, $C_1$–$C_4$-alkylcarbonyloxy, $C_1$–$C_4$-alkoxycarbonyl, aryl or aryloxy, where the cyclic substituents, in turn, can have attached to them one to three of the following substituents: halogen, nitro, cyano, $C_1$–$C_4$-alkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylsulfonyl, $C_1$–$C_4$-alkylsulfoxy, $C_1$–$C_4$-alkylsulfonyloxy, $C_1$–$C_4$-alkylcarbonyl, $C_1$–$C_4$-alkylcarbonyloxy, $C_1$–$C_4$-alkoxycarbonyl, aryl, aryloxy;

preferably aryl, it being possible for these radicals to have attached to them one to three of the following groups: nitro, halogen, cyano, $C_1$–$C_4$-alkyl, $C_1$–$C_4$-alkoxy, $C_1$–$C_4$-haloalkoxy, $C_1$–$C_4$-alkylthio, phenyl, phenyloxy.

Compounds I which are furthermore preferred are those where $R^1$ and $R^3$ have the following meanings: $R^1$ and $R^3$=halogen, $C_1$–$C_3$-alkyl.

Especially preferred with a view to their use are the compounds Ic which are compiled in the tables which follow, and their hydrochlorides and N-oxides.

TABLE 1

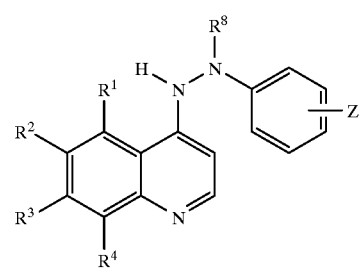

$R^5, R^6 = H$
$R^8 = H$

Ic

| No. | $R_1$ | $R_2$ | $R_3$ | $R_4$ | Z |
|---|---|---|---|---|---|
| 12.1 | H | H | Cl | H | 2-F |
| 12.2 | H | H | Cl | H | 2-Cl |
| 12.3 | H | H | Cl | H | 2-Br |
| 12.4 | H | H | Cl | H | 2-CN |
| 12.5 | H | H | Cl | H | 2-$CF_3$ |
| 12.6 | H | H | Cl | H | 2-$NO_2$ |
| 12.7 | H | H | Cl | H | 2-t-Bu |
| 12.8 | H | H | Cl | H | 2-$CH_3$ |
| 12.9 | H | H | Cl | H | 2-$OCH_3$ |
| 12.10 | H | H | Cl | H | 3-F |
| 12.11 | H | H | Cl | H | 3-Cl |
| 12.12 | H | H | Cl | H | 3-$CF_3$ |
| 12.13 | H | H | Cl | H | 3-CN |
| 12.14 | H | H | Cl | H | 3-$OCH_3$ |
| 12.15 | H | H | Cl | H | 3-Ph |
| 12.16 | H | H | Cl | H | 4-F |
| 12.17 | H | H | Cl | H | 4-Cl |
| 12.18 | H | H | Cl | H | 4-Br |
| 12.19 | H | H | Cl | H | 4-$CF_3$ |
| 12.20 | H | H | Cl | H | 4-$CH_3$ |
| 12.21 | H | H | Cl | H | 4-C($CH_3$)$_3$ |
| 12.22 | H | H | Cl | H | 4-CH($CH_3$)$_2$ |
| 12.23 | H | H | Cl | H | 4-CN |
| 12.24 | H | H | Cl | H | 2,4-di-F |
| 12.25 | H | H | Cl | H | 2-Cl-4-F |
| 12.26 | H | H | Cl | H | 2,4-di-Br |
| 12.27 | H | H | Cl | H | 2,4-di-$NO_2$ |
| 12.28 | H | H | Cl | H | 2-$CH_3$-4-F |
| 12.29 | H | H | Cl | H | 2,6-di-F |
| 12.30 | H | H | Cl | H | 2,4,6-tri-$CH_3$ |
| 12.31 | F | H | H | H | 4-F |
| 12.32 | Cl | H | H | H | 4-F |
| 12.33 | $NO_2$ | H | H | H | 4-F |
| 12.34 | H | F | H | H | 4-F |
| 12.35 | H | Cl | H | H | 4-F |
| 12.36 | H | $CH_3$ | H | H | 4-F |
| 12.37 | H | $NO_2$ | H | H | 4-F |
| 12.38 | H | $OC_2H_5$ | H | H | 4-F |
| 12.39 | H | H | F | H | 4-F |
| 12.40 | H | H | Cl | H | 4-F |
| 12.41 | H | H | Br | H | 4-F |
| 12.42 | H | H | $NO_2$ | H | 4-F |
| 12.43 | H | H | $OCF_3$ | H | 4-F |
| 12.44 | H | H | $C_2H_5$ | H | 4-F |
| 12.45 | H | H | $SCF_3$ | H | 4-F |
| 12.46 | H | H | O—$C_2H_5$ | H | 4-F |
| 12.47 | H | H | H | F | 4-F |
| 12.48 | H | H | H | Cl | 4-F |
| 12.49 | H | H | H | $CF_3$ | 4-F |
| 12.50 | F | H | F | H | 4-F |
| 12.51 | Cl | H | Cl | H | 4-F |
| 12.52 | $CH_3$ | H | $CH_3$ | H | 4-F |
| 12.53 | O—$CH_3$ | H | O—$CH_3$ | H | 4-F |
| 12.54 | Cl | F | H | H | 4-F |
| 12.55 | Cl | Cl | H | H | 4-F |
| 12.56 | Cl | $CH_3$ | H | H | 4-F |
| 12.57 | H | Br | H | Cl | 4-F |
| 12.58 | H | Cl | H | OH | 4-F |
| 12.59 | H | O—$CH_3$ | H | $NO_2$ | 4-F |
| 12.60 | H | F | Cl | H | 4-F |
| 12.61 | H | $CH_3$ | Cl | H | 4-F |
| 12.62 | H | H | Cl | Cl | 4-F |
| 12.63 | Cl | H | H | Cl | 4-F |
| 12.64 | Cl | F | Cl | H | 4-F |
| 12.65 | H | H | Cl | CN | 4-F |
| 12.66 | Cl | $CH_3$ | Cl | H | 4-F |
| 12.67 | Cl | Cl | Cl | H | 4-F |
| 12.68 | Cl | Cl | Cl | Cl | 4-F |
| 12.69 | H | H | H | Cl | 2-Cl-4F |
| 12.70 | H | H | H | Cl | 2-F-4-Br |
| 12.71 | H | H | H | Cl | 2,3-di-$CH_3$ |
| 12.72 | H | H | H | Cl | 2-F-4-Cl |
| 12.73 | H | H | H | Cl | 2,4-di-Cl-6-F |
| 12.74 | H | H | H | Cl | 2,4-di-F |
| 12.75 | H | H | H | Cl | 2,4-di-$CH_3$ |
| 12.76 | H | H | H | Cl | 2-$C_2H_5$ |
| 12.77 | H | H | H | Cl | 2-$CH_3$-4-F |
| 12.78 | H | H | H | Cl | 3-$CH_3$-4-Cl |
| 12.79 | H | H | Cl | H | H |
| 12.80 | H | H | Cl | H | 3-$CH_3$ |
| 12.81 | H | H | Cl | H | 3-Br |
| 12.82 | H | H | Cl | H | 3-$NO_2$ |
| 12.83 | H | H | Cl | H | 4-$NO_2$ |
| 12.84 | H | H | Cl | H | 2-Cl-6-F |
| 12.85 | H | H | Cl | H | 2,3-di-$CH_3$ |
| 12.86 | H | H | Cl | H | 2,4-di-$CH_3$ |
| 12.87 | H | H | Cl | H | 2,5-di-$CH_3$ |
| 12.88 | H | H | Cl | H | 2,5-di-F |
| 12.89 | H | H | Cl | H | 2-$NO_2$-4-CN |
| 12.90 | H | H | Cl | H | 2-CN-3-Cl |
| 12.91 | H | H | Cl | H | 3-CN |
| 12.92 | H | H | Cl | H | 2,3-di-Cl |
| 12.93 | H | H | Cl | H | 2,5-di-Cl |
| 12.94 | H | H | Cl | H | 2,4,6-tri-Cl |
| 12.95 | H | H | Cl | H | 2,3,4-tri-Cl |
| 12.96 | H | H | Cl | H | 2-Cl-4-$CF_3$ |
| 12.97 | H | H | Cl | H | 2,6-di-Cl |
| 12.98 | H | H | Cl | H | 2-Cl-5-$CF_3$ |
| 12.99 | H | H | Cl | H | 2-Cl-6-$CH_3$ |

TABLE 1-continued

Structure Ic with R⁵, R⁶ = H; R⁸ = H

| No. | R₁ | R₂ | R₃ | R₄ | Z |
|---|---|---|---|---|---|
| 12.100 | H | H | Cl | H | 2-CH₃-4-Cl |
| 12.101 | H | H | Cl | H | 2,4-di-Cl |
| 12.102 | H | H | Cl | H | 3,4-di-Cl |
| 12.103 | H | H | Cl | H | 3,5-di-Cl |
| 12.104 | H | H | Cl | H | 3,4-di-CH₃ |
| 12.105 | H | H | Cl | H | 3,5-di-CH₃ |
| 12.106 | H | H | Cl | H | 3-Cl-4-CH₃ |
| 12.107 | H | H | Cl | H | 3-Cl-4--F |
| 12.108 | H | H | Cl | H | 3,5-di-CF₃ |
| 12.109 | H | H | Cl | H | 3-CF₃-6-CH₃S |
| 12.110 | H | H | Cl | H | 2-CH₃-5-F |
| 12.111 | H | H | Cl | H | 4-CF₃O |
| 12.112 | H | H | Cl | H | 2-C₂H₅ |
| 12.113 | H | H | Cl | H | 2,6-di-Cl-4-CF₃ |
| 12.114 | H | H | Cl | H | 3-Cl-6-CH₃ |
| 12.115 | H | H | Cl | H | 2-CN-3-F |
| 12.116 | H | H | Cl | H | 2-O—CH₂—C₆H₅ |
| 12.117 | H | H | Cl | H | 4-NO₂ |
| 12.118 | H | H | Cl | H | 4-OCH₃ |
| 12.119 | H | H | Cl | H | 4-SO₂CH₃ |
| 12.120 | Cl | H | Cl | H | H |
| 12.121 | Cl | H | Cl | H | 3-CH₃ |
| 12.122 | Cl | H | Cl | H | 3-Br |
| 12.123 | Cl | H | Cl | H | 3-NO₂ |
| 12.124 | Cl | H | Cl | H | 4-NO₂ |
| 12.125 | Cl | H | Cl | H | 2-Cl-6-F |
| 12.126 | Cl | H | Cl | H | 2,3-di-CH₃ |
| 12.127 | Cl | H | Cl | H | 2,4-di-CH₃ |
| 12.128 | Cl | H | Cl | H | 2,5-di-CH₃ |
| 12.129 | Cl | H | Cl | H | 2,5-di-F |
| 12.130 | Cl | H | Cl | H | 2-NO₂-4-CN |
| 12.131 | Cl | H | Cl | H | 2-CN-3-Cl |
| 12.132 | Cl | H | Cl | H | 3-CN |
| 12.133 | Cl | H | Cl | H | 2,3-di-Cl |
| 12.134 | Cl | H | Cl | H | 2,5-di-Cl |
| 12.135 | Cl | H | Cl | H | 2,4,6-tri-Cl |
| 12.136 | Cl | H | Cl | H | 2,3,4-tri-Cl |
| 12.137 | Cl | H | Cl | H | 2-Cl-4-CF₃ |
| 12.138 | Cl | H | Cl | H | 2,6-di-Cl |
| 12.139 | Cl | H | Cl | H | 2-Cl-5-CF₃ |
| 12.140 | Cl | H | Cl | H | 2-Cl-6-CH₃ |
| 12.141 | Cl | H | Cl | H | 2-CH₃-4-Cl |
| 12.142 | Cl | H | Cl | H | 2,4-di-Cl |
| 12.143 | Cl | H | Cl | H | 3,4-di-Cl |
| 12.144 | Cl | H | Cl | H | 3,5-di-Cl |
| 12.145 | Cl | H | Cl | H | 3,4-di-CH₃ |
| 12.146 | Cl | H | Cl | H | 3,5-di-CH₃ |
| 12.147 | Cl | H | Cl | H | 3-Cl-4-CH₃ |
| 12.148 | Cl | H | Cl | H | 3-Cl-4--F |
| 12.149 | Cl | H | Cl | H | 3,5-di-CF₃ |
| 12.150 | Cl | H | Cl | H | 3-CF₃-6-CH₃S |
| 12.151 | Cl | H | Cl | H | 2-CH₃-5-F |
| 12.152 | Cl | H | Cl | H | 4-CF₃O |
| 12.153 | Cl | H | Cl | H | 2-C₂H₅ |
| 12.154 | Cl | H | Cl | H | 2,6-di-Cl-4-CF₃ |
| 12.155 | Cl | H | Cl | H | 3-Cl-6-CH₃ |
| 12.156 | Cl | H | Cl | H | 2-CN-3-F |
| 12.157 | Cl | H | Cl | H | 2-O—CH₂—C₆H₅ |
| 12.158 | Cl | H | Cl | H | 4-NO₂ |
| 12.159 | Cl | H | Cl | H | 4-OCH₃ |
| 12.160 | Cl | H | Cl | H | 4-SO₂CH₃ |
| 12.161 | Cl | H | Cl | H | 2-F |
| 12.162 | Cl | H | Cl | H | 2-Cl |
| 12.163 | Cl | H | Cl | H | 2-Br |
| 12.164 | Cl | H | Cl | H | 2-CN |
| 12.165 | Cl | H | Cl | H | 2-CF₃ |
| 12.166 | Cl | H | Cl | H | 2-NO₂ |
| 12.167 | Cl | H | Cl | H | 2-t-Bu |
| 12.168 | Cl | H | Cl | H | 2-CH₃ |
| 12.169 | Cl | H | Cl | H | 2-OCH₃ |
| 12.170 | Cl | H | Cl | H | 3-F |
| 12.171 | Cl | H | Cl | H | 3-Cl |
| 12.172 | Cl | H | Cl | H | 3-CF₃ |
| 12.173 | Cl | H | Cl | H | 3-CN |
| 12.174 | Cl | H | Cl | H | 3-OCH₃ |
| 12.175 | Cl | H | Cl | H | 3-Ph |
| 12.176 | Cl | H | Cl | H | 4-F |
| 12.177 | Cl | H | Cl | H | 4-Cl |
| 12.178 | Cl | H | Cl | H | 4-Br |
| 12.179 | Cl | H | Cl | H | 4-CF₃ |
| 12.180 | Cl | H | Cl | H | 4-CH₃ |
| 12.181 | Cl | H | Cl | H | 4-C(CH₃)₃ |
| 12.182 | Cl | H | Cl | H | 4-CH(CH₃)₂ |
| 12.183 | Cl | H | Cl | H | 4-CN |
| 12.184 | Cl | H | Cl | H | 2,4-di-F |
| 12.185 | Cl | H | Cl | H | 2-Cl-4-F |
| 12.186 | Cl | H | Cl | H | 2,4-di-Br |
| 12.187 | Cl | H | Cl | H | 2,4-di-NO₂ |
| 12.188 | Cl | H | Cl | H | 2-CH₃-4-F |
| 12.189 | Cl | H | Cl | H | 2,6-di-F |
| 12.190 | Cl | H | Cl | H | 2,4,6-tri-CH₃ |
| 12.191 | H | H | H | Cl | H |
| 12.192 | H | H | F | H | H |

Furthermore, especially preferred compounds are those of the formula Ic below:

the compounds 1.1a–1.192a, which differ from the corresponding compounds 1.1–1.192 of Table 1 by the fact that the substituent $R^8$ is $CH_3$.

the compounds 1.1b–1.192b, which differ from the corresponding compounds 1.1–1.192 of Table 1 by the fact that the substituent $R^8$ is $C_2H_5$.

the compounds 1.1c–1.192c, which differ from the corresponding compounds 1.1–1.192 of Table 1 by the fact that the substituent $R^8$ is i—$C_3H_7$.

the compounds 1.1d–1.192d, which differ from the corresponding compounds 1.1–1.192 of Table 1 by the fact that the substituent $R^8$ is c—$C_5H_9$.

the compounds 1.1e–1.192e, which differ from the corresponding compounds 1.1–1.192 of Table 1 by the fact that the substituent $R^8$ is $CH_2$—$C_6H_5$.

the compounds 1.1f–1.192f, which differ from the corresponding compounds 1.1–1.192 of Table 1 by the fact that the substituent $R^8$ is $COCH_3$.

TABLE 2

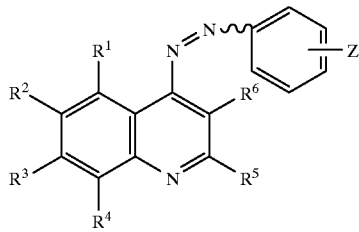

$R^5, R^6 = H$

| No. | $R_1$ | $R_2$ | $R_3$ | $R_4$ | Z |
|---|---|---|---|---|---|
| 2.193 | H | H | Cl | H | 2-Cl |
| 2.194 | H | H | Cl | H | 2-Br |
| 2.195 | H | H | Cl | H | 2-CN |
| 2.196 | H | H | Cl | H | 2-CF$_3$ |
| 2.197 | H | H | Cl | H | 2-NO$_2$ |
| 2.198 | H | H | Cl | H | 2-t-Bu |
| 2.199 | H | H | Cl | H | 2-CH$_3$ |
| 2.200 | H | H | Cl | H | 2-OCH$_3$ |
| 2.201 | H | H | Cl | H | 3-F |
| 2.202 | H | H | Cl | H | 3-Cl |
| 2.203 | H | H | Cl | H | 3-CF$_3$ |
| 2.204 | H | H | Cl | H | 3-CN |
| 2.205 | H | H | Cl | H | 3-OCH$_3$ |
| 2.206 | H | H | Cl | H | 3-Ph |
| 2.207 | H | H | Cl | H | 4-F |
| 2.208 | H | H | Cl | H | 4-Cl |
| 2.209 | H | H | Cl | H | 4-Br |
| 2.210 | H | H | Cl | H | 4-CF$_3$ |
| 2.211 | H | H | Cl | H | 4-CH$_3$ |
| 2.212 | H | H | Cl | H | 4-C(CH$_3$)$_3$ |
| 2.213 | H | H | Cl | H | 4-CH(CH$_3$)$_2$ |
| 2.214 | H | H | Cl | H | 4-CN |
| 2.215 | H | H | Cl | H | 2,4-di-F |
| 2.216 | H | H | Cl | H | 2-Cl-4-F |
| 2.217 | H | H | Cl | H | 2,4-di-Br |
| 2.218 | H | H | Cl | H | 2,4-di-NO$_2$ |
| 2.219 | H | H | Cl | H | 2-CH$_3$-4-F |
| 2.220 | H | H | Cl | H | 2,6-di-F |
| 2.221 | H | H | Cl | H | 2,4,6-tri-CH$_3$ |
| 2.222 | F | H | H | H | 4-F |
| 2.223 | Cl | H | H | H | 4-F |
| 2.224 | NO$_2$ | H | H | H | 4-F |
| 2.225 | H | F | H | H | 4-F |
| 2.226 | H | Cl | H | H | 4-F |
| 2.227 | H | CH$_3$ | H | H | 4-F |
| 2.228 | H | NO$_2$ | H | H | 4-F |
| 2.229 | H | OC$_2$H$_5$ | H | H | 4-F |
| 2.230 | H | H | F | H | 4-F |
| 2.231 | H | H | Cl | H | 4-F |
| 2.232 | H | H | Br | H | 4-F |
| 2.233 | H | H | NO$_2$ | H | 4-F |
| 2.234 | H | H | OCF$_3$ | H | 4-F |
| 2.235 | H | H | C$_2$H$_5$ | H | 4-F |
| 2.236 | H | H | SCF$_3$ | H | 4-F |
| 2.237 | H | H | O—C$_2$H$_5$ | H | 4-F |
| 2.238 | H | H | H | F | 4-F |
| 2.239 | H | H | H | Cl | 4-F |
| 2.240 | H | H | H | CF$_3$ | 4-F |
| 2.241 | F | H | F | H | 4-F |
| 2.242 | Cl | H | Cl | H | 4-F |
| 2.243 | CH$_3$ | H | CH$_3$ | H | 4-F |
| 2.244 | O—CH$_3$ | H | O—CH$_3$ | H | 4-F |
| 2.245 | Cl | F | H | H | 4-F |
| 2.246 | Cl | Cl | H | H | 4-F |
| 2.247 | Cl | CH$_3$ | H | H | 4-F |
| 2.248 | H | Br | H | Cl | 4-F |
| 2.249 | H | Cl | H | OH | 4-F |
| 2.250 | H | O—CH$_3$ | H | NO$_2$ | 4-F |
| 2.251 | H | F | Cl | H | 4-F |
| 2.252 | H | CH$_3$ | Cl | H | 4-F |
| 2.253 | H | H | Cl | Cl | 4-F |
| 2.254 | Cl | H | H | Cl | 4-F |
| 2.255 | Cl | F | Cl | H | 4-F |

TABLE 2-continued

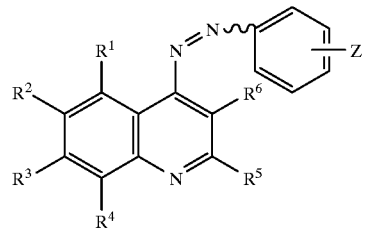

$R^5, R^6 = H$

| No. | $R_1$ | $R_2$ | $R_3$ | $R_4$ | Z |
|---|---|---|---|---|---|
| 2.256 | H | H | Cl | CN | 4-F |
| 2.257 | Cl | CH$_3$ | Cl | H | 4-F |
| 2.258 | Cl | Cl | Cl | H | 4-F |
| 2.259 | Cl | Cl | Cl | Cl | 4-F |
| 2.260 | H | H | H | Cl | 2-Cl-4F |
| 2.261 | H | H | H | Cl | 2-F-4-Br |
| 2.262 | H | H | H | Cl | 2,3-di-CH$_3$ |
| 2.263 | H | H | H | Cl | 2-F-4-Cl |
| 2.264 | H | H | H | Cl | 2,4-di-Cl-6-F |
| 2.265 | H | H | H | Cl | 2,4-di-F |
| 2.266 | H | H | H | Cl | 2,4-di-CH$_3$ |
| 2.267 | H | H | H | Cl | 2-C$_2$H$_5$ |
| 2.268 | H | H | H | Cl | 2-CH$_3$-4-F |
| 2.269 | H | H | H | Cl | 3-CH$_3$-4-Cl |
| 2.270 | H | H | Cl | H | H |
| 2.271 | H | H | Cl | H | 3-CH$_3$ |
| 2.272 | H | H | Cl | H | 3-Br |
| 2.273 | H | H | Cl | H | 3-NO$_2$ |
| 2.274 | H | H | Cl | H | 4-NO$_2$ |
| 2.275 | H | H | Cl | H | 2-Cl-6-F |
| 2.276 | H | H | Cl | H | 2,3-di-CH$_3$ |
| 2.277 | H | H | Cl | H | 2,4-di-CH$_3$ |
| 2.278 | H | H | Cl | H | 2,5-di-CH$_3$ |
| 2.279 | H | H | Cl | H | 2,5-di-F |
| 2.280 | H | H | Cl | H | 2-NO$_2$-4-CN |
| 2.281 | H | H | Cl | H | 2-CN-3-Cl |
| 2.282 | H | H | Cl | H | 3-CN |
| 2.283 | H | H | Cl | H | 2,3-di-Cl |
| 2.284 | H | H | Cl | H | 2,5-di-Cl |
| 2.285 | H | H | Cl | H | 2,4,6-tri-Cl |
| 2.286 | H | H | Cl | H | 2,3,4-tri-Cl |
| 2.287 | H | H | Cl | H | 2-Cl-4-CF$_3$ |
| 2.288 | H | H | Cl | H | 2,6-di-Cl |
| 2.289 | H | H | Cl | H | 2-Cl-5-CF$_3$ |
| 2.290 | H | H | Cl | H | 2-Cl-6-CH$_3$ |
| 2.291 | H | H | Cl | H | 2-CH$_3$-4-Cl |
| 2.292 | H | H | Cl | H | 2,4-di-Cl |
| 2.293 | H | H | Cl | H | 3,4-di-Cl |
| 2.294 | H | H | Cl | H | 3,5-di-Cl |
| 2.295 | H | H | Cl | H | 3,4-di-CH$_3$ |
| 2.296 | H | H | Cl | H | 3,5-di-CH$_3$ |
| 2.297 | H | H | Cl | H | 3-Cl-4-CH$_3$ |
| 2.298 | H | H | Cl | H | 3-Cl-4--F |
| 2.299 | H | H | Cl | H | 3, 5-di-CF$_3$ |
| 2.300 | H | H | Cl | H | 3-CF$_3$-6-CH$_3$S |
| 2.301 | H | H | Cl | H | 2-CH$_3$-5-F |
| 2.302 | H | H | Cl | H | 4-CF$_3$O |
| 2.303 | H | H | Cl | H | 2-C$_2$H$_5$ |
| 2.304 | H | H | Cl | H | 2,6-di-Cl-4-CF$_3$ |
| 2.305 | H | H | Cl | H | 3-Cl-6-CH$_3$ |
| 2.306 | H | H | Cl | H | 2-CN-3-F |
| 2.307 | H | H | Cl | H | 2-O—CH$_2$—C$_6$H$_5$ |
| 2.308 | H | H | Cl | H | 4-NO$_2$ |
| 2.309 | H | H | Cl | H | 4-OCH$_3$ |
| 2.310 | H | H | Cl | H | 4-SO$_2$CH$_3$ |
| 2.311 | Cl | H | Cl | H | H |
| 2.312 | Cl | H | Cl | H | 3-CH$_3$ |
| 2.313 | Cl | H | Cl | H | 3-Br |
| 2.314 | Cl | H | Cl | H | 3-NO$_2$ |
| 2.315 | Cl | H | Cl | H | 4-NO$_2$ |
| 2.316 | Cl | H | Cl | H | 2-Cl-6-F |
| 2.317 | Cl | H | Cl | H | 2,3-di-CH$_3$ |
| 2.318 | Cl | H | Cl | H | 2,4-di-CH$_3$ |

TABLE 2-continued

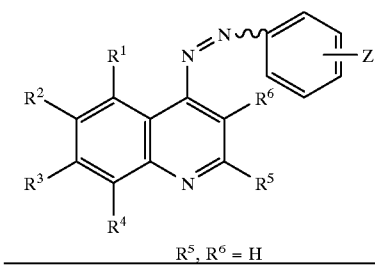

$R^5, R^6 = H$

| No. | $R_1$ | $R_2$ | $R_3$ | $R_4$ | Z |
|---|---|---|---|---|---|
| 2.319 | Cl | H | Cl | H | 2,5-di-CH₃ |
| 2.320 | Cl | H | Cl | H | 2,5-di-F |
| 2.321 | Cl | H | Cl | H | 2-NO₂-4-CN |
| 2.322 | Cl | H | Cl | H | 2-CN-3-Cl |
| 2.323 | Cl | H | Cl | H | 3-CN |
| 2.324 | Cl | H | Cl | H | 2,3-di-Cl |
| 2.325 | Cl | H | Cl | H | 2,5-di-Cl |
| 2.326 | Cl | H | Cl | H | 2,4,6-tri-Cl |
| 2.327 | Cl | H | Cl | H | 2,3,4-tri-Cl |
| 2.328 | Cl | H | Cl | H | 2-Cl-4-CF₃ |
| 2.329 | Cl | H | Cl | H | 2,6-di-Cl |
| 2.330 | Cl | H | Cl | H | 2-Cl-5-CF₃ |
| 2.331 | Cl | H | Cl | H | 2-Cl-6-CH₃ |
| 2.332 | Cl | H | Cl | H | 2-CH₃-4-Cl |
| 2.333 | Cl | H | Cl | H | 2,4-di-Cl |
| 2.334 | Cl | H | Cl | H | 3,4-di-Cl |
| 2.335 | Cl | H | Cl | H | 3,5-di-Cl |
| 2.336 | Cl | H | Cl | H | 3,4-di-CH₃ |
| 2.337 | Cl | H | Cl | H | 3,5-di-CH₃ |
| 2.338 | Cl | H | Cl | H | 3-Cl-4-CH₃ |
| 2.339 | Cl | H | Cl | H | 3-Cl-4-F |
| 2.340 | Cl | H | Cl | H | 3,5-di-CF₃ |
| 2.341 | Cl | H | Cl | H | 3-CF₃-6-CH₃S |
| 2.342 | Cl | H | Cl | H | 2-CH₃-5-F |
| 2.343 | Cl | H | Cl | H | 4-CF₃O |
| 2.344 | Cl | H | Cl | H | 2-C₂H₅ |
| 2.345 | Cl | H | Cl | H | 2,6-di-Cl-4-CF₃ |
| 2.346 | Cl | H | Cl | H | 3-Cl-6-CH₃ |
| 2.347 | Cl | H | Cl | H | 2-CN-3-F |
| 2.348 | Cl | H | Cl | H | 2-O—CH₂—C₆H₅ |
| 2.349 | Cl | H | Cl | H | 4-NO₂ |
| 2.350 | Cl | H | Cl | H | 4-OCH₃ |
| 2.351 | Cl | H | Cl | H | 4-SO₂CH₃ |
| 2.352 | Cl | H | Cl | H | 2-F |
| 2.353 | Cl | H | Cl | H | 2-Cl |
| 2.354 | Cl | H | Cl | H | 2-Br |
| 2.355 | Cl | H | Cl | H | 2-CN |
| 2.356 | Cl | H | Cl | H | 2-CF₃ |
| 2.357 | Cl | H | Cl | H | 2-NO₂ |
| 2.358 | Cl | H | Cl | H | 2-t-Bu |
| 2.359 | Cl | H | Cl | H | 2-CH₃ |
| 2.360 | Cl | H | Cl | H | 2-OCH₃ |
| 2.361 | Cl | H | Cl | H | 3-F |
| 2.362 | Cl | H | Cl | H | 3-Cl |
| 2.363 | Cl | H | Cl | H | 3-CF₃ |
| 2.364 | Cl | H | Cl | H | 3-CN |
| 2.365 | Cl | H | Cl | H | 3-OCH₃ |
| 2.366 | Cl | H | Cl | H | 3-Ph |
| 2.367 | Cl | H | Cl | H | 4-F |
| 2.368 | Cl | H | Cl | H | 4-Cl |
| 2.369 | Cl | H | Cl | H | 4-Br |
| 2.370 | Cl | H | Cl | H | 4-CF₃ |
| 2.371 | Cl | H | Cl | H | 4-CH₃ |
| 2.372 | Cl | H | Cl | H | 4-C(CH₃)₃ |
| 2.373 | Cl | H | Cl | H | 4-CH(CH₃)₂ |
| 2.374 | Cl | H | Cl | H | 4-CN |
| 2.375 | Cl | H | Cl | H | 2,4-di-F |
| 2.376 | Cl | H | Cl | H | 2-Cl-4-F |
| 2.377 | Cl | H | Cl | H | 2,4-di-Br |
| 2.378 | Cl | H | Cl | H | 2,4-di-NO₂ |
| 2.379 | Cl | H | Cl | H | 2-CH₃-4-F |
| 2.380 | Cl | H | Cl | H | 2,6-di-F |
| 2.381 | Cl | H | Cl | H | 2,4,6-tri-CH₃ |

TABLE 2-continued

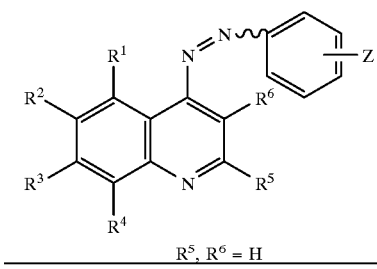

$R^5, R^6 = H$

| No. | $R_1$ | $R_2$ | $R_3$ | $R_4$ | Z |
|---|---|---|---|---|---|
| 2.382 | H | H | H | Cl | H |
| 2.383 | H | H | F | Cl | H |
| 2.384 | H | H | Cl | H | 2-F |

The novel compounds of the formula I are suitable as fungicides.

The novel compounds, or the compositions comprising them, can be employed for example in the form of ready-to-spray solutions, powders, suspensions, also highly concentrated aqueous, oily or other suspensions or dispersions, emulsions, oil dispersions, pastes, dusts, materials for spreading or granules or by means of spraying, atomizing, dusting, spreading or pouring. The use forms depend on the intended aims; in any case, they should guarantee the finest possible distribution of the active ingredients according to the invention.

Normally, the plants are sprayed or dusted with the active ingredients, or the seeds of the plants are treated with the active ingredients.

The formulations are prepared in a known manner, eg. by extending the active ingredient with solvents and/or carriers, if desired using emulsifiers and dispersants, it also being possible to use other organic solvents and auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers, such as non-ionic and anionic emulsifiers (eg. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols and of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated iso-octyl-, octyl- or nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powder or other solid carriers.

Examples of such preparations are:

I. a solution of 90 parts by weight of a compound I according to the invention and 10 parts by weight of N-methyl-2-pyrrolidone, which is suitable for use in the form of microdrops;

II. a mixture of 10 parts by weight of a compound I according to the invention, 70 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water;

III. an aqueous dispersion of 10 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. an aqueous dispersion of 10 parts by weight of a compound I according to the invention, 25 parts by weight of cyclohexanone, 55 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of a preferably solid compound I according to the invention, 3 parts by weight of sodium di-isobutylnaphthalene-α-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 62 parts by weight of pulverulent silica gel and 8 parts by weight of paraffin oil which has been sprayed onto the surface of this silica gel; this preparation imparts good adherence properties to the active ingredient;

VIII. a stable aqueous dispersion of 40 parts by weight of a compound I according to the invention, 10 parts by weight of the sodium salt of a phenolsulfonic acid/urea/ formaldehyde condensate, 2 parts by weight of silica gel and 48 parts by weight of water, and this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/ formaldehyde condensate and 50 parts by weight of a paraffinic mineral oil.

The novel compounds are distinguished by an outstanding efficacy against a broad spectrum of phytopathogenic fungi, in particular from the classes of the Deuteromycetes, Ascomycetes, Phycomycetes and Basidiomycetes. Some of them act systemically and can be employed as foliar- and soil-acting fungicides.

They are especially important for controlling a large number of fungi in a variety of crop plants such as wheat, rye, barley, oats, rice, maize, lawns, cotton, soya, coffee, sugar cane, grapevines, fruit species, ornamentals and vegetable species such as cucumbers, beans and cucurbits, and on the seeds of these plants.

The compounds are applied by treating the fungi, or the seeds, plants, materials or the soil to be protected against fungal infection, with a fungicidally active amount of the active ingredient.

Application is effected before or after infection of the materials, plants or seeds with the fungi.

The novel compounds are specifically suitable for controlling the following plant diseases:

Erysiphe graminis (powdery mildew) in cereals, Erysiphe cichoracearum and Sphaerotheca fuliginea in cucurbits, Podosphaera leucotricha in apples, Uncinula necator in grapevines, Puccinia species in cereals, Rhizoctonia species in cotton and lawns, Ustilago species in cereals and sugar cane, Venturia inaequalis (scab) in apples, Helminthosporium species in cereals, Septoria nodorum in wheat, Botrytis cinerea (gray mold) in strawberries, grapevines, ornamentals and vegetables, Cercospora arachidicola in groundnuts, Pseudocercosporella herpotrichoides in wheat and barley, Pyricularia oryzae in rice, Phytophthora infestans in potatoes and tomatoes, Fusarium and Verticillium species in various plants, Plasmopara viticola in grapevines and Alternaria species in vegetables and fruit.

The novel compounds can also be employed in the protection of materials (protection of wood), eg. against Paecilomyces variotii.

In general, the fungicidal compositions comprise from 0.1 to 95, preferably from 0.5 to 90, % by weight of active ingredient.

Depending on the nature of the desired effect, the rates of application are from 0.025 to 2, preferably 0.1 to 1 kg, of active ingredient per ha.

In the treatment of seed, amounts of from 0.001 to 50, preferably 0.01 to 10 g, of active ingredient are generally required per kilogram of seed.

In the use form as fungicides, the agents according to the invention can also be present together with other active ingredients, eg. herbicides, insecticides, growth regulators, fungicides or else fertilizers.

A mixture with fungicides in many cases results in a widening of the fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives such as dinitro(1-methylheptyl)phenyl crotonate, 2-sec-butyl-4,6-dinitrophenyl 3,3-dimethyl acrylate, 2-sec-butyl-4,6-dinitrophenyl isopropylcarbonate, diisopropyl 5-nitro-isophthalate;

heterocyclic substances such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo[4,5-b] quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanomethylthiobenzothiazole, 1,4-dichloro-2,5-dimethoxybenzene, 4-(2-chlorophenylhydrazono)-3-methyl-5-isoxazolone, pyridine-2-thione 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxylic cyclohexylamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, 1-[3-(2-chlorophenyl)-1-(4-fluorophenyl)oxiran-2-ylmethyl]-1H-1,2,4-triazole and a variety of fungicides such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-furoyl(2)-DL-alaninate, methyl N-(2,6-dimethylphenyl)-N-(2'-methoxyacetyl)-DL-alaninate, N-(2,6-dimethylphenyl)-N-chloroacetyl-D, L-2-aminobutyrolactone, methyl N-(2,6-dimethylphenyl)-N-(phenylacetyl)-DL-alaninate, 5-methyl-5-vinyl-3-(3,5-dichlorophenyl)-2,4-dioxo-1, 3-oxazolidine, 3-[(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1, 2-dicarboximide, 2-cyano-[N-(ethylaminocarbonyl)-2-methoximino]-acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2, 6-dinitro-4-trifluoromethylphenyl)-5-trifluoromethyl-3-chloro-2-aminopyridine, 1-((bis-(4-fluorophenyl) methylsilyl)methyl)-1H-1,2,4-triazole, strobilurins such as methyl E-methoximino-[α-(o-tolyloxy)-o-tolyl]acetate, methyl E-2-{2-[6-(2-cyanophenoxy)pyridimin-4-yloxy]phenyl}-3-methoxyacrylate, N-methyl-E-methoximino-[α-(2,5-dimethyloxy)-o-tolyl]acetamide.

Anilinopyrimidines such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl)aniline.

Phenylpyrroles such as 4-(2,2-difluoro-1,3-benzodioxol-4-yl)pyrrole-3-carbonitrile.

Cinnamamides such as

N-morpholinyl-3-(4-chlorophenyl)-3-(3,4-dimethoxyphenyl)-acrylamide.

7-Chloro-4-(N'-(3-fluorophenylhydrazino)quinoline hydrochloride 5 g (0.026 mol) of 4,7-dichloroquinoline, 4.72 g (0.029 mol) of 3-fluorophenylhydrazine hydrochloride are refluxed in 50 ml of i-butanol until starting compound can no longer be detected (HPLC check).

After cooling, the precipitate which has formed is filtered off with suction, washed with diisopropyl ether and dried. This gives 5.9 g (70%) of the title compound.

7-Chloro-4-(3-fluorophenylazo)quinoline 4.34 g (0.027 mol) of iron(III) chloride are added to 3.6 g (0.011 mol) of 7-chloro-4-(N'-(3-fluorophenylhydrazino) quinoline hydrochloride in 50 ml of glacial acetic acid and the mixture is refluxed for 30 minutes. After cooling, it is poured into 500 ml of ice-water and brought to a pH of 10 using ammonium hydroxide solution. The resulting precipitate is filtered off with suction and extracted repeatedly using ethanol. The ethanolic phase is treated with water and the resulting precipitate is filtered off with suction.

1.6 g (51%) of the azo compound are obtained (m.p. 145–147°)

TABLE 3

(Physical data: IR [cm$^{-1}$], $^{13}$C [ppm against tetramethylsilane], m.p. [° C.])

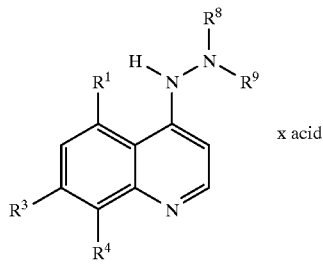

x acid

| No. | R$_1$ | R$_3$ | R$_4$ | R$_8$ | R$_9$ | Acid | IR [cm$^{-1}$]; $^{13}$C (atom); m.p. (° C.) |
|---|---|---|---|---|---|---|---|
| 3.1 | H | Cl | H | H | 2-fluorophenyl | HCl | 157.4 (C-4) |
| 3.2 | H | Cl | H | H | 2-methylphenyl | HCl | 157.4 (C-4) |
| 3.3 | H | Cl | H | H | 2-chlorophenyl | HCl | 157.3 (C-4) |
| 3.4 | H | Cl | H | H | 2-bromophenyl | HCl | >240° |
| 3.5 | H | Cl | H | H | 3-chlorophenyl | HCl | >240° |
| 3.6 | H | Cl | H | H | 3-fluorophenyl | HCl | >240° |
| 3.7 | H | Cl | H | H | 4-chlorophenyl | HCl | 3180, 2916, 1621, 1583, 1492, 1448, 1211, 864, 825 |
| 3.8 | H | Cl | H | H | 4-fluorophenyl | HCl | >240° |
| 3.9 | H | Cl | H | H | 4-methylphenyl | HCl | 3160, 2747, 1616, 1584, 1449, 1208, 819 |
| 3.10 | H | Cl | H | H | 4-tert-butyl-phenyl | HCl | |
| 3.11 | H | Cl | H | H | phenyl | HCl | >240° |
| 3.12 | H | Cl | H | H | 2,4-dimethyl-phenyl | HCl | 157.3 (C-4) |
| 3.13 | H | Cl | H | H | 2,4,6-tri-chlorophenyl | HCl | >240° |
| 3.14 | H | Cl | H | CH$_3$ | phenyl | HCl | >240° |
| 3.15 | H | Cl | H | H | 2-chlorophenyl | HCl | >240° |
| 3.16 | H | Cl | H | H | 3-trifluoro-methylphenyl | HCl | >240° |
| 3.17 | H | CF$_3$ | H | H | 4-chlorophenyl | HCl | |
| 3.18 | H | H | Cl | H | 2-fluorophenyl | HCl | |
| 3.19 | Cl | Cl | H | H | 4-fluorophenyl | HCl | |
| 3.20 | H | Cl | H | CH$_3$ | 2-chlorophenyl | HCl | |
| 3.21 | Cl | Cl | H | H | 2-methylphenyl | HCl | |
| 3.22 | CH$_3$ | CH$_3$ | H | H | 2-chlorophenyl | HCl | |
| 3.23 | H | H | Cl | H | phenyl | HCl | |
| 3.24 | H | F | H | H | 4-chlorophenyl | HCl | |
| 3.25 | H | CH$_3$ | H | H | 4-chlorophenyl | HCl | |
| 3.26 | H | Cl | H | H | 4-chlorophenyl | HOOCCOOH | |
| 3.27 | H | Cl | H | H | 4-chlorophenyl | p-CH$_3$—C$_6$H$_4$—SO$_3$H | |
| 3.28 | Cl | Cl | H | H | 4-chlorophenyl | HCl | 3060, 2800, 1608, 1584, 1546, 1487, 1399, 870, 644 |
| 3.29 | Cl | Cl | H | H | 2-chlorophenyl | HCl | 157 (C-4) |
| 3.30 | Cl | Cl | H | H | 3-trifluoro-methyl-5-chlorophenyl | HCl | 183–184° |
| 3.31 | H | H | Cl | H | 2-chlorophenyl | HCl | >240° |

TABLE 4

Ih

Structure: Quinoline with R3 at 7-position, NH-NH linkage to 2-pyridyl with Z substituent $R^1, R^2, R^4, R^5, R^6, R^7, R^8 = H$

| No. | $R^3$ | Z | m.p. [° C.] |
|---|---|---|---|
| 6.1 | Cl | 2-F-3-CF$_3$-5-Cl | 216–218 |
| 6.2 | Cl | 2-OCH$_3$-3-Cl-5-CF$_3$ | 130–132 |
| 6.3 | Cl | 2-Cl-3-CF$_3$-5-Cl | 265 |
| 6.4 | Cl | 3-CF$_3$-5-Cl | 222–225 |
| 6.5 | Cl | 3-CF$_3$ | 162–165 |
| 6.6 | Cl | 3,5-di-CF$_3$ | 180 |
| 6.7 | Cl | 3-Cl-5-CF$_3$ | 198–201 |
| 6.8 | Cl | 2-CF$_3$ | 176–180 |
| 6.9 | Cl | 2-CH$_3$-4-CF$_3$ | 199–201 |

TABLE 5

Ii $R^2, R^4, R^5, R^6, R^7, R^8 = H$

| No. | $R^1$ | $R^3$ | Z | m.p. [° C.] |
|---|---|---|---|---|
| 7.1 | Cl | Cl | 3-CF$_3$-5-Cl | 183–184 |
| 7.2 | Cl | Cl | 3-CF$_3$ | 165–167 |

TABLE 6

Ij $R^2, R^4, R^5, R^6, R^7, R^8 = H$

| No. | $R^1$ | $R^3$ | Z | m.p. [° C.] |
|---|---|---|---|---|
| 8.1 | Cl | Cl | 4-Cl | 183–186 |
| 8.2 | H | Cl | 4-Cl | 211–213 |

TABLE 7

(Physical data: IR [cm$^{-1}$], $^{13}$C [ppm against tetramethylsilane], m.p. [° C.])

| No. | $R^1$ | $R^3$ | $R^4$ | $R^9$ | m.p. [°] |
|---|---|---|---|---|---|
| 7.1 | H | Cl | H | 2-chlorophenyl | 160–163 |
| 7.2 | H | Cl | H | 2-fluorophenyl | 133–135 |
| 7.3 | H | Cl | H | 3-fluorophenyl | 145–147 |
| 7.4 | H | Cl | H | 4-methylphenyl | 103–105 |
| 7.5 | H | Cl | H | 4-fluorophenyl | 159–160 |
| 7.6 | H | Cl | H | 4-chlorophenyl | 163–165 |
| 7.7 | H | Cl | H | phenyl | 105–108 |
| 7.8 | H | Cl | H | 2-methylphenyl | 94–96 |
| 7.9 | H | Cl | H | 3-chlorophenyl | 120–122 |
| 7.10 | H | H | Cl | phenyl | 139–141 |
| 7.11 | CH$_3$ | CH$_3$ | H | 4-methylphenyl | 138–140 |
| 7.12 | H | F | H | 4-fluorophenyl | 102–104 |
| 7.13 | H | F | H | 4-fluorophenyl | 122–124 |
| 7.14 | H | F | H | 4-chlorophenyl | 167–168 |
| 7.15 | H | CH$_3$ | H | 4-chlorophenyl | 92–94 |
| 7.16 | H | CH$_3$ | H | 4-fluorophenyl | 96–98 |
| 7.17 | Cl | Cl | H | 2-chlorophenyl | 186–188 |
| 7.18 | Cl | Cl | H | 4-chlorophenyl | 188–189 |
| 7.19 | H | CF$_3$ | H | 4-chlorophenyl | 170–173 |
| 7.20 | H | H | Cl | 2-chlorophenyl | 160–162 |
| 7.21 | H | H | Cl | 4-chlorophenyl | 204–205 |
| 7.22 | H | H | Cl | 2-fluorophenyl | 165–167 |
| 7.23 | CH$_3$ | CH$_3$ | H | 4-chlorophenyl | 164–166 |
| 7.24 | CH$_3$ | CH$_3$ | H | 4-fluorophenyl | 117–118 |
| 7.25 | CH$_3$ | CH$_3$ | H | 2-chlorophenyl | 114–116 |
| 7.26 | Cl | Cl | H | 2-fluorophenyl | 160–163 |
| 7.27 | H | Cl | H | 2,4,6-trichlorophenyl | 191–193 |

TABLE 7-continued (Physical data: IR [cm$^{-1}$], $^{13}$C [ppm against tetramethylsilane], m.p. [° C.]

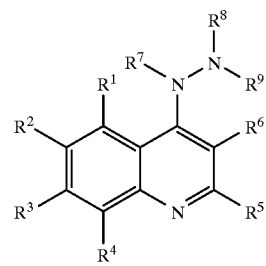

| No. | R$^1$ | R$^3$ | R$^4$ | R$^9$ | m.p. [°] |
|---|---|---|---|---|---|
| 7.28 | Cl | Cl | H | 2-methylphenyl | 118–120 |
| 7.29 | H | Cl | H | 3-trifluoromethyl-phenyl | 121–123 |
| 7.30 | H | Cl | H | 2,4-dimethylphenyl | 114–116 |
| 7.31 | Cl | Cl | H | 4-fluorophenyl | 128–130 |
| 7.32 | H | Cl | H | 2-bromophenyl | 157–159 |
| 7.33 | H | Cl | H | 4-chlorophenyl | 168–170$^1$) |
| 7.34 | H | Cl | H | 4-fluorophenyl | 177–178$^1$) |
| 7.35 | H | Cl | H | 4-chlorophenyl | 136–139$^2$) |
| 7.36 | H | Cl | H | 4-chlorophenyl | 180–183$^3$) |

$^1$) N-Oxide on the nitrogen atom "*"
$^2$) N-Oxide on the nitrogen atom "**"
$^3$) N-Oxide on the nitrogen atom "*" and on the nitrogen atom "**"

USE EXAMPLE 1

Activity against powdery mildew of wheat

Leaves of wheat seedlings cv. "Frühgold" which had been grown in pots were sprayed with an aqueous spray mixture comprising 80% of active ingredient and 20% of emulsifier in the dry matter and, 24 hours after the spray coating had dried, dusted with oidia (spores) of powdery mildew of wheat (Erysiphe graminis var. tritici). The test plants were subseqently placed in the greenhouse at from 20 to 22° C. and a relative atmospheric humidity of from 75 to 80%. After 7 days, the extent of mildew development was determined.

Scoring:

The infected leaf area is indicated as a percentage.

TABLE 10

| Active ingredient | % infection of the leaves after application of aqueous preparation of active ingredient in ppm | | |
|---|---|---|---|
| No. 1.17 | 63 | 16 | 4 ppm |
|  | 0 | 1 | 8 |
| Untreated | — | 80 | — |

We claim:
1. A quinoline compound of formula I

$$\text{(I)}$$

where the substituents have the following meanings:
R$^1$, R$^2$, R$^3$, R$^4$ in each case independently of one another are hydrogen, hydroxyl, nitro, halogen, C$_1$–C$_4$-alkyl, C$_1$–C$_4$-alkoxy, C$_1$–C$_4$-haloalkyl, C$_1$–C$_4$-alkylthio, C$_1$–C$_4$-haloalkoxy, C$_1$–C$_4$-haloalkylthio, C$_1$–C$_4$-alkoxyalkyl, provided at least two groups among R$^1$, R$^2$, R$^3$ and R$^4$ are non-hydrogen, R$^5$, R$^6$ in each case independently of one another are hydrogen, halogen, C$_1$–C$_4$-alkyl, C$_1$–C$_4$-alkoxy, C$_1$–C$_4$-haloalkoxy, C$_1$–C$_4$-alkylthio;

R$^7$ is hydrogen,

R$^8$ is hydrogen, methyl, or

R$^7$ and R$^8$ together form a bond;

R$^9$ is phenyl or monocyclic N-heterocycles, each possibly substituted by one to three of the following groups: halogen, C$_1$–C$_4$-alkyl, C$_1$–C$_4$-haloalkyl, C$_1$–C$_4$-alkoxy, or an N-oxide or acid addition salt of a quinoline of the formula I, with the exception of the compounds where the substituents are defined as follows:

1 a–d R$^{1,2,3,4,5,6,7,8}$=H; R$^9$=C$_6$H$_5$, 4-Cl—C$_6$H$_4$, 2,4-di-Cl—C$_6$H$_3$, 2,4-di-BR—C$_6$H$_3$, 1 e–h R$^{1,2,3,4,5,6,7,8}$=H; R$^9$=4-Cl—C$_6$H$_4$, 2,4-di-Cl—C$_6$H$_3$, in each case in the form of the N-oxide and the HCl salt, 1 i R$^{1,2,3,4,5,6,7,8}$=H; R$^9$=4-Br—C$_6$H$_4$ HBr salt 1 j–k R$^{1,2,3,4,6,8}$=H; R$^5$=CH$_3$; R$^7$=H; R$^9$=C$_6$H$_5$ 1 m R$^{1,2,3,4,6,7,8}$=H; R$^{2,5}$=CH$_3$; R$^9$=C$_6$H$_5$, 1 n R$^1$=O—CH$_3$; R$^{2\ 3,4,6,7,8}$=H; R$^5$=CH$_3$; R$^9$=C$_6$H$_5$ HCl salt, 1 r–s R$^{1,2,3,4,5,6,7,8}$=H; R$^3$=Cl; R$^9$=4-NO$_2$-C$_6$H$_4$, 4-Cl—C$_6$H$_4$ 1 t–u R$^{1,2,3,4,6,7,8}$=H; R$^5$=Cl; R$^9$=4-Cl—C$_6$H$_4$, 2,4-di-Cl—C$_6$H$_3$ 1 z R$^{1,2,4,5,6,7,8}$=H; R$^3$=Cl; R$^9$=CH$_2$=3=Py, 2 d–o R$^{1,2,3,4,5,6}$=H; R$^9$=C$_6$H$_5$, C$_6$H$_5$ N-oxide, 4-Cl—C$_6$H$_4$, 4-Cl—C$_6$H$_4$ N-oxide, 4-Br—C$_6$H$_4$, 4-Br—C$_6$H$_4$ N-oxide, 2, 4-Cl—C$_6$H$_3$, 2, 4-Br—C$_6$H$_3$, 2, 4-Br—C$_6$H$_3$ N-oxide, 4-(CH$_3$)$_2$N—C$_6$H$_4$, 4-(CH$_3$)$_2$N—C$_6$H$_4$ N-oxide, 2 p–q R$^{1,3,6}$=H; R$^5$=CH$_3$, R$^9$=C$_6$H$_5$; R$^2$=OCH$_3$, R$^4$=OCH$_3$;

2 r–s R$^{1,3,6}$=H; R$^5$=CH$_3$; R$^9$=C$_6$H$_5$; R$^2$=OCH$_2$CH$_3$; R$^4$=OCH$_2$CH$_3$;

2 t–v R$^{1,2,3,4,6}$=H; R$^5$=Cl; R$^9$=C$_6$H$_5$, 4-Cl—C$_6$H$_4$, 2, 4-Cl—C$_6$H$_3$;

2 w R$^{1,2,4,5,6}$=H; R$^3$=Cl; R$^9$=C$_6$H$_5$, 2 x R$^{1,2,3,4,6}$=H; R$^5$=CH$_3$; R$^9$=C$_6$H$_5$, 2 y R$^{1,2,3,4}$=H; R$^{5,6}$=CH$_3$; R$^9$=C$_6$H$_5$, 2 z R$^{2,3,4,6}$=H; R$^{1,5}$=CH$_3$; R$^9$=C$_6$H$_5$, 3 a R$^{1,3,4,6}$=H; R$^{2,5}$=CH$_3$; R$^9$=C$_6$H$_5$, 3 b $R^{1,2,3,6}$=H; $R^{4,5}$=CH$_3$; $R^9$=C$_6$H$_5$,
3 c $R^{2,4,6}$=H; $R^{1,3,5}$=CH$_3$; $R^9$=C$_6$H$_5$,
3d $R^{1,3,6}$=H; $R^{2,4,5}$=CH$_3$; $R^9$=C$_6$H$_5$,
4 a $R^{1,2,3,6,7,8}$=H; $R^4$=OCH$_3$, $R^5$=CH$_3$, $R^9$=C$_6$H$_5$.

2. A quinoline compound of the formula I as claimed in claim 1, where the substituents have the following meanings:

$R^1$, $R^2$, $R^3$, $R^4$ in each case independently of one another are hydrogen, halogen, C$_1$–C$_4$-alkyl, C$_1$–C$_4$-alkoxy, C$_1$–C$_4$-haloalkyl, C$_1$–C$_4$-alkylthio, C$_1$–C$_4$-haloalkoxy, C$_1$–C$_4$-haloalkylthio, C$_1$–C$_4$-alkoxyalkyl, $R^5$, $R^6$ in each case independently of one another are hydrogen, C$_1$–C$_2$-alkyl or halogen;

$R^7$ is hydrogen;

$R^8$ is hydrogen, methyl; or $R^7$, $R^8$ together form a bond;

$R^9$ is phenyl or monocyclic N-heterocycles, it being possible for these radicals to have attached to them one to three of the following groups: halogen, C$_1$–C$_4$-alkyl, C$_1$–C$_4$-haloalkyl, C$_1$–C$_4$-alkoxy.

3. A quinoline compound of the formula I as claimed in claim 1, where the substituent $R^3$ has the following meanings:

$R^3$ is cyano, halogen, C$_1$–C$_3$-alkyl, C$_1$–C$_3$-alkyloxy, C$_1$–C$_3$-alkylthio, C$_1$–C$_3$-haloalkoxy.

4. A quinoline compound of the formula I as claimed in claim 1, where the substituents $R^1$ and $R^3$ have the following meanings:

$R^1$ and $R^3$=halogen, C$_1$–C$_3$-alkyl.

5. A quinoline compound of the formula I as claimed in claim 1, where two of the substituents $R^1$, $R^2$, $R^3$ or $R^4$ are hydrogen.

6. A quinoline compound of the formula Ia as claimed in claim 1,

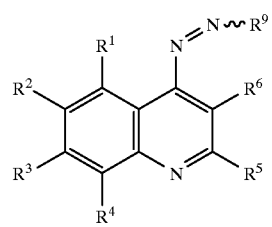
Ia where the substituents $R^1$, $R^2$, $R^3$, $R^4$, $R^5$, $R^6$ and $R^9$ have the meanings given in claim 1.

7. A quinoline compound of the formula Ia as claimed in claim 6, where the substituents have the following meanings:

$R^1$, $R^2$, $R^3$, $R^4$ in each case independently of one another are hydrogen, halogen, C$_1$–C$_4$-alkyl, C$_1$–C$_4$-alkoxy, C$_1$–C$_4$-haloalkyl, C$_1$–C$_4$-alkylthio, C$_1$–C$_4$-haloalkoxy, C$_1$–C$_4$-haloalkylthio, C$_1$–C$_4$-alkoxyalkyl;

$R^5$ and $R^6$ in each case independently of one another are hydrogen, C$_1$–C$_2$-alkyl or halogen;

$R^9$ is phenyl or monocyclic N-heterocycles, it being possible for these radicals to have attached to them one to three of the following groups: halogen, C$_1$–C$_4$-alkyl, C$_1$–C$_4$-alkoxy.

8. A process for the preparation of the quinolines of the formula I as claimed in claim 1, which comprises reacting 4-halogenquinolines of the formula II with hydrazines of the formula III,

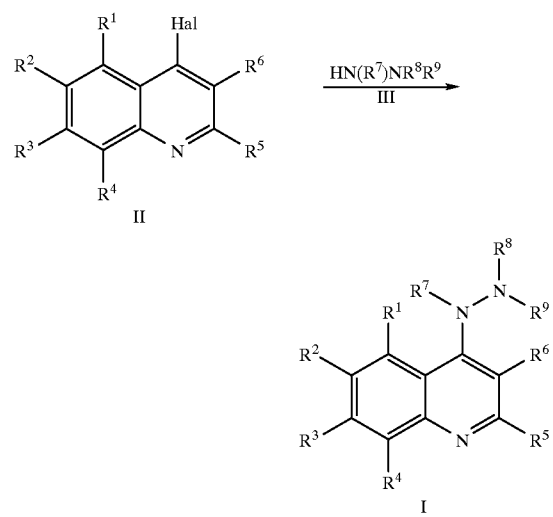

the substituents $R^1$ to $R^9$ having the meaning given in claim 1 and Hal being I, Br, Cl or F.

9. A process for the preparation of the quinolines of claim 6, which comprises oxidizing the quinolines of the formula Ib with an oxidant,

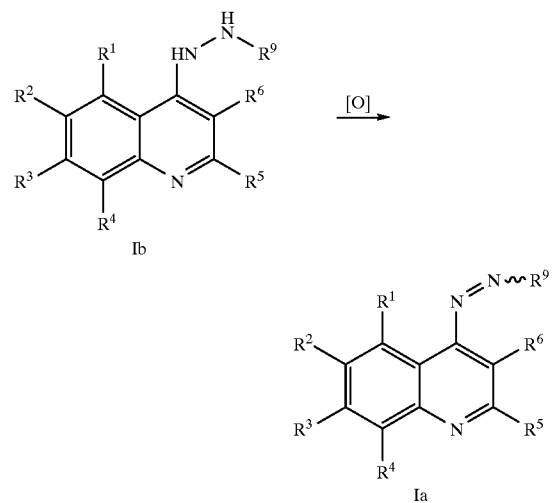

wherein the substituents $R^1$, $R^2$, $R^3$, $R^4$, $R^5$, $R^6$ and $R^9$ are as defined above.

10. A fungicidal composition comprising a fungicidally active amount of at least one quinoline of the formula I or of one of its N-oxides or acid addition salts as claimed in claim 1, with the exception of the compounds 1a to 3d.

11. A method of controlling harmful fungi, which comprises treating the harmful fungi, their environment, or the plants, areas, materials or spaces to be kept free from them with a fungicidally active amount of a compound of the general formula I or of one of its N-oxides or acid addition salts as claimed in claim 1, including the compounds 1a to 3d.

12. A method of controlling harmful fungi, which comprises treating the harmful fungi, their environment, or the plants, areas, materials or spaces to be kept free from them with a fungicidally active amount of a fungicidal composition comprising a quinoline of the formula I as claimed in claim 10.

* * * * *